United States Patent [19]

Walker

[11] Patent Number: 4,691,074

[45] Date of Patent: Sep. 1, 1987

[54] MONOCHLOROBIPHENYL:CUPROUS ALUMINUM TETRACHLORIDE

[76] Inventor: David G. Walker, 904 Fleetwood Dr., Baytown, Tex. 77520

[21] Appl. No.: 767,321

[22] Filed: Jun. 17, 1985

Related U.S. Application Data

[62] Division of Ser. No. 591,128, Mar. 12, 1984, abandoned.

[51] Int. Cl.$^4$ .................. C07C 7/148; C07C 7/10; C07C 7/156
[52] U.S. Cl. .................. 585/849; 585/843; 585/848; 55/63; 55/68; 55/73
[58] Field of Search .................. 585/848, 849; 55/68, 55/63, 73, 40

[56] References Cited

U.S. PATENT DOCUMENTS

| | | | |
|---|---|---|---|
| 3,440,296 | 4/1969 | Walker | 585/849 |
| 3,441,377 | 4/1969 | Sawyer et al. | 585/849 |
| 3,480,662 | 11/1969 | Carr, Jr. et al. | 585/849 |
| 3,592,865 | 7/1971 | Long et al. | 585/848 |
| 3,647,843 | 3/1972 | Walker et al. | 585/848 |
| 3,651,159 | 3/1972 | Long et al. | 585/848 |
| 3,754,047 | 8/1973 | Long et al. | 585/848 |
| 3,758,606 | 9/1973 | Horowitz et al. | 585/848 |
| 3,767,725 | 10/1973 | Walker et al. | 585/848 |
| 3,776,972 | 12/1973 | Tyler, III et al. | 585/848 |
| 3,923,958 | 12/1975 | Turnbo et al. | 585/848 |
| 3,933,878 | 1/1976 | Tyler, III et al. | 585/848 |
| 3,960,910 | 6/1976 | Sudduth et al. | 585/848 |
| 4,525,180 | 6/1985 | Hirai et al. | 585/848 |

FOREIGN PATENT DOCUMENTS

0591445  2/1978  U.S.S.R. .................. 585/848

*Primary Examiner*—Andrew H. Metz
*Assistant Examiner*—Helane Myers

[57] ABSTRACT

A compound, monochloro biphenyl: $CuAlCl_4$, has been isolated and proven to exist. Monochloro biphenyl can be any one of the possible three isomers, ortho, meta and para or can be any mixture of the three isomers.

An improved process is provided for the separation of olefins, acetylenes, carbon monoxide or hydrogen sulfide from gaseous feedstreams. A solvent is made by dissolving $CuAlCl_4$ in a liquid mixture of monochloro biphenyls. This solvent is used to contact the gas feedstream and dissolve by complexation the ligand part of the feedstream. The ligand-fat solvent is separated from the gas feedstream and the ligand recovered by running the solvent through an atmospheric reboiler and one or more reboilers under vacuum. The gas streams of the reboilers are combined and after cooling are a nearly pure stream of the separated ligand.

Solutions of $CuAlCl_4$ in monochloro biphenyls are a low-viscosity, high ligand-solubility and rapid-equilibrating solvent for the separation of ligands (olefins, acetylenes, carbon monoxide and hydrogen sulfide).

4 Claims, 1 Drawing Figure

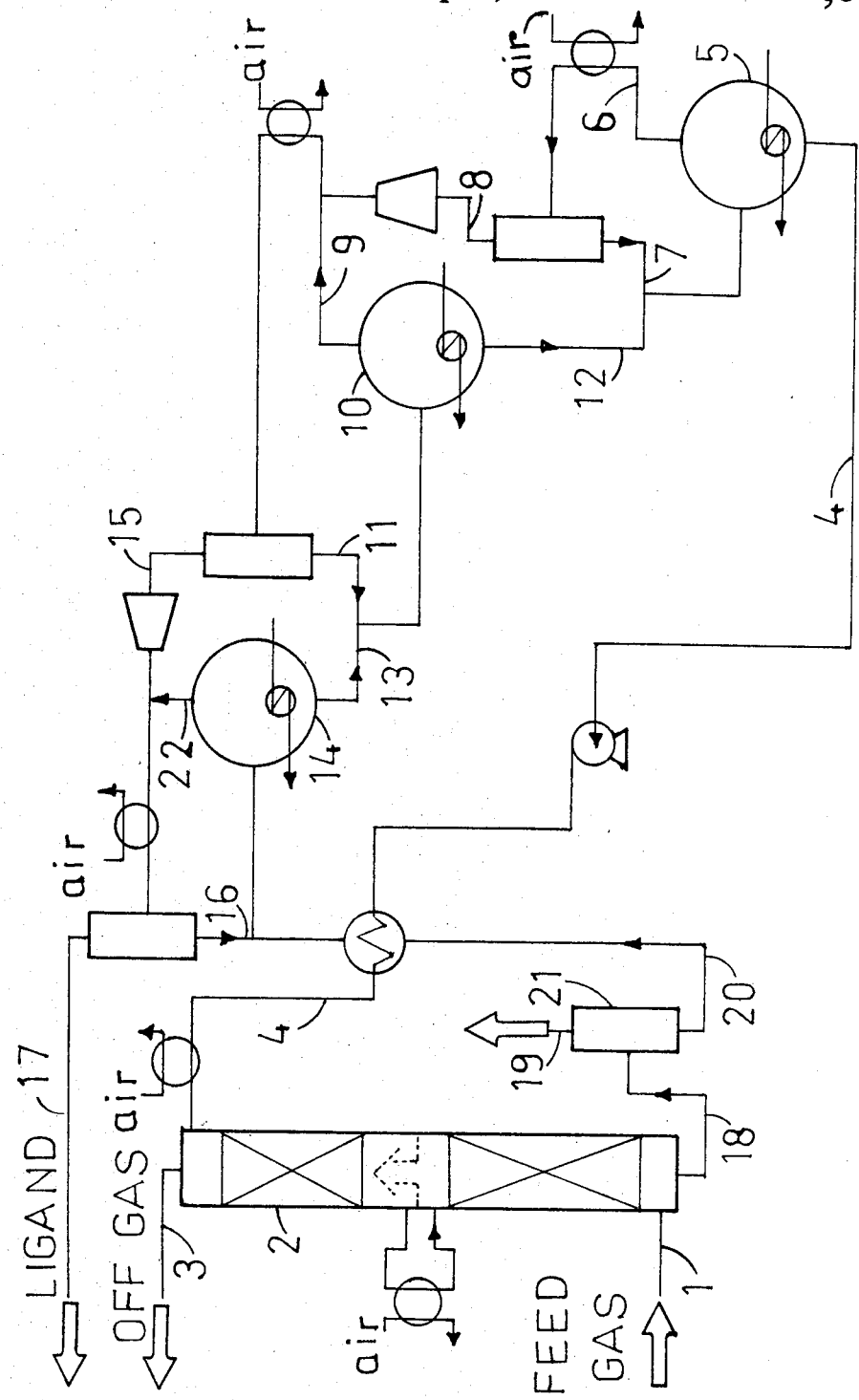

MONOCHLOROBIPHENYL:CUPROUS ALUMINUM TETRACHLORIDE

This is a divisional of Application Ser. No. 591,128 filed 03/12/84, now abandoned.

PRIOR ART

U.S. Pat. Nos. 3,651,159 and 3,592,865 describe the preparation and use of cuprous aluminum tetrachloride when dissolved in aromatic solutions to separate gaseous ligands like olefins, acetylenes, carbon monoxide and aromatics. Benzene and toluene are among the aromatic compounds described as useful for this service. A drawback of these two aromatics and many others is that these compounds have substantial vapor pressure at ambient temperature. Because of this important amounts of these aromatics vaporize into the ligand-poor gas as well as the ligand gas product. Additional expensive process steps are necessary to separate and recover the vaporized aromatic from these gas stream products of the separation.

U.S. Pat. No. 3,754,047 claims to be an improvement in the operation of the above mentioned patents. This patent uses a solvent which is a solution of $CuAlCl_4$ in a mixed aromatic liquid. The mixed aromatic liquid has a major amount of a multi-ringed high boiling aromatic and a minor amount of a strongly complexing, high boiling single-ringed aromatic. Due to the very low vapor pressure of these aromatics at ambient temperature, no process steps are necessary to recover these aromatics from the ligand-poor gas and the product gas of the separation process. Experiments by the author of this patent application show that the mass transfer properties of these solutions is poor. In addition most all of the aromatics claimed are unstable in the presence of $CuAlCl_4$ at 100° C. This instability limits the practical worth of the solvent solutions claimed in this patent. (U.S. Pat. No. 3,754,047).

SUMMARY OF THE INVENTION

A compound of the empirical formula, $C_{12}H_9Cl:CuAlCl_4$, has been found to exist. It is a crystalline solid at ambient temperature. The chloro-biphenyl ($C_{12}H_9Cl$) part of the compound may be any of the three possible isomers (ortho, meta and para) but may also be any possible mixture of the isomers of monochloro biphenyl.

Solutions of the above compound in monochloro biphenyl liquids are excellent solvents for the separation of olefins, acetylenes, carbon monoxide and hydrogen sulfide from gases by reversible complexing.

Dissolved olefins, acetylenes, carbon monoxide and hydrogen sulfide are recovered from these solvents by passing the ligand rich solvent through a series of reboilers. One reboiler operates at from 1.0 to 1.6 atma pressure while the other reboilers operate from 0.1 to 1.0 atma pressure. The combined gas product streams from the reboilers are cooled to produce a nearly pure ligand product (olefins, acetylenes, carbon monoxide and hydrogen sulfide).

EMBODIMENT OF THE INVENTION

The present invention is illustrated by the following examples.

EXAMPLE 1:

$CuAlCl_4$ was mixed and heated with enough monochloro biphenyl isomer mixture to form a homogeneous solution 3M in Cu. Upon cooling the hot mixture to ambient temperature a solid phase crystallized out. The solid was separated from the liquid and washed twice with cold pentane to remove absorbed liquids. The resulting solid was analyzed. Monochloro biphenyl and $CuAlCl_4$ were found in a nearly one to one molecular ratio.

$CuAlCl_4$ was dissolved in an isomeric mixture of methyl biphenyls with heating. Upon cooling to ambient temperature, a solid again precipitated. The solid was again washed with cold pentane and analyzed. Methyl biphenyl was found in a one to two molecular ratio with $CuAlCl_4$.

EXAMPLE 2

A 2.2 Molar solution in $Cu^{+1}$ was made by dissolving anhydrous $CuAlCl_4$ in an isomeric mixture of monochloro biphenyls. A solution of the same $Cu^{+1}$ strength was made by dissolving $CuAlCl_4$ in an isomeric mixture of methyl biphenyls.

The monochloro biphenyl based solvent was found to equilibrate with a stirred aliquote of carbon monoxide gas in five minutes at ambient temperature. The methyl biphenyl based solvent required more than two hours to equlibrate with carbon monoxide under identical experimental conditions.

The carbon monoxide solubility was 30% greater in the monechloro biphenyl based solvent than for the methyl biphenyl one. (ambient temperature and CO partial pressure=200 mm Hg)

Explanation of the Efficacy of Monochloro biphenyl

Alkyl substituted biphenyls like methyl biphenyl behave toward $Cu^{+1}$ like a benzene and a toluene compound. Both have an important complexing ability toward the cuprous cation. The resulting solvent species is then, methyl biphenyl: 2 $CuAlCl_4$, The high molecular weight species is viscous and slow to rearrange and dissolve a ligand like carbon monoxide by complexing.

Monochloro biphenyl behaves toward $Cu^{+1}$ like a benzene and a chloro benzene compound. Chloro benzene itself has only a small solubility for $CuAlCl_4$. The solvent species in monochloro biphenyl is chloro biphenyl: $CuAlCl_4$. This lower molecular weight species gives solutions of relatively low viscosity and excellent ligand complexing speeds.

All biphenyl compounds, unsubstituted or with alkyl groups, form viscous solutions with $CuAlCl_4$ which have poor mass transfer speeds. Dichloro biphenyls, as normally made, contain one chloro group on each phenyl ring. These compounds have only a weak solubility for $CuAlCl_4$. Monochloro biphenyl, on the other hand, is unique in having a reasonably high solubility for $CuAlCl_4$ (2.2 Molar at 25° C.) and also excellent mass transfer properties similar to benzene or toluene.

Monochloro biphenyl mixtures are best used pure for making $CuAlCl_4$ solutions as ligand complexing solvents. Any addition of long chain alkyl benzenes, naphthalenes or alkylated biphenyls is harmful to the solvent's worth as a reversible complexing solvent.

PREFERRED EMBODIMENT OF THE INVENTION

Stripper columns, normally used with solvents based on water or with constituents boiling from 100° to 140° C., are not useful with a solvent of monochloro bipheny and $CuAlCl_4$. The vapor pressure of monochloro biphenyls are so low at temperatures below 150° C. that little monochloro biphenyl vaporizes in an atmospheric stripper column.

The accompanying drawing is a process flow diagram of the preferred method of separating and producing a ligand from a gas using the solvent of this invention.

A practical way to use this type of solvent is pictured in the accompanying drawing and herewith described below.

A ligand containing feedstream 1 is fed to the bottom of an absorber column 2. The absorber has two or more contacting sections and one or more solvent intercoolers to remove the heat of ligand complexation. Gas rises through the absorber where it contacts the solvent (a solution of $CuAlCl_4$ in monochloro biphenyl) 4. which is fed into the top of the absorber 2. Ligand-poor gas 3 flows from the absorber overhead and exits the process. Ligand-fat solvent 18 accumulates in the absorber bottom 2 and flows to a flash tank 21. The flash tank 21 is operated at a lower pressure and may also contain a heating coil to raise the solvent's temperature. A flash gas stream 19 which is relatively rich in the non-ligand part of the feed gas 1 exits the process. The flashed ligand-rich solvent 20 flows from the flash tank 21 through a cross-heat exchanger and feeds into reboiler 14. Reboiler 14 operates at 130° C. and 1 to 1.5 atma pressure.

Lean hot solvent 4 is the liquid product of reboiler 5. Reboiler 5 operates at 130° C. and 0.1 to 0.3 atma pressure. The lean solvent 4 is cross heat exchanged and trim cooled before feeding into the absorber 2.

Reboiler 5 makes as a gas product 6 which is cooled to split into a liquid 7 and a gas 8. The liquid 7 is recycled to the reboiler. The gas 8 is compressed and mixed with 9, the vapor product of reboiler 10.

Reboiler 10 operates at 130° C. and 0.3 to 0.9 atma pressure. The liquid product 12 of reboiler 10 feeds reboiler 5. The vapor product 9 is cooled to make a liquid 11 and a gas 15. The liquid 11 is recycled to the reboiler. The gas 15 is compressed and mixed with the vapor product 22 of reboiler 14. These combined gases 22+15 are cooled to make a liquid 16 and a gas product 17 which is nearly pure ligand (or ligands). Liquid 16 is recycled to the reboiler 14.

Heat is supplied to the three reboilers (14, 10 and 5) to keep the solvent at its specified temperature. Normally, 70% or more of the ligand product is made in reboiler 14. The rest of the ligand product is made from the two vacuum reboilers 10 and 5.

What is claimed is:

1. A process for separating a complexible ligand, selected from the group consisting of $C_2$ to $C_5$ olefins, $C_2$ to $C_5$ acetylenes, carbon monoxide and hydrogen sulfide, from a feedstream containing the ligand which consists essentially of contacting the feedstream with a liquid solution of cuprous aluminum tetrachloride ($CuAlCl_4$) in $C_{12}H_9Cl$ (an isomer or mixture of isomers of monochlorobiphenyl); said contacting being conducted under conditions to form a complex of the ligand and the solution from the feedstream while the complexed ligand is regenerated from the solvent by passing the ligand-rich solvent successively through the atmospheric reboiler (1 to 1.6 atma) pressure and one or more vacuum reboilers (0.1 to 0.9 atma pressure), whereas the gaseous streams from the reboilers are combined and cooled to yield the separated pure liquid.

2. The process of claim 1 where the ligand is ethylene or propylene.

3. The process of claim 1 where the ligand is carbon monoxide.

4. The process of claim 1 where the ligand is hydrogen sulfide.

* * * * *